United States Patent [19]

Sengewald

[11] Patent Number: 4,884,694
[45] Date of Patent: Dec. 5, 1989

[54] GAS-STERILIZABLE PACKAGE, COVER OF AND ARRANGEMENT FOR PRODUCING THE SAME

[76] Inventor: Karl-Heinz Sengewald, 4802 Halle, Westf. 1, Fed. Rep. of Germany

[21] Appl. No.: 213,615

[22] Filed: Jun. 30, 1988

Related U.S. Application Data

[63] Continuation-in-part of Ser. No. 901,027, Aug. 27, 1986, abandoned.

[30] Foreign Application Priority Data

Aug. 27, 1985 [DE] Fed. Rep. of Germany ....... 3530484
Jul. 12, 1986 [DE] Fed. Rep. of Germany ....... 3623568

[51] Int. Cl.⁴ ............................................. B65D 5/64
[52] U.S. Cl. ............................. 206/484.1; 206/484.2; 206/439; 206/524.2; 206/524.4; 206/631; 428/354; 428/34.2; 428/34.3
[58] Field of Search ................... 206/439, 484.1, 484.2, 206/524.2, 524.4, 631, 484; 428/35, 354

[56] References Cited

U.S. PATENT DOCUMENTS

| | | | |
|---|---|---|---|
| 3,061,087 | 10/1962 | Scrivens et al. | 206/439 |
| 3,435,948 | 4/1969 | Kaganov et al. | 206/439 |
| 4,055,672 | 10/1977 | Hirsch et al. | 206/484 X |
| 4,270,658 | 6/1981 | Schuster | 206/484.1 X |
| 4,469,258 | 9/1984 | Wright et al. | 206/631 X |
| 4,537,305 | 8/1985 | Takanashi | 206/524.2 X |
| 4,673,601 | 6/1987 | Lamping et al. | 206/631 X |

Primary Examiner—William Price
Attorney, Agent, or Firm—Michael J. Striker

[57] ABSTRACT

A package to be gas-sterilizable comprises a lower foil composed of a thermoplastic material and having an edge, an upper gas-permeable foil having an edge, the lower foil and the upper foil being connected with one another in the region of the edges, an intermediate gas-permeable foil arranged to protect the upper foil from a content of the package, located between the upper and lower foils and loosely extending over the upper foil, the intermediate foil being perforated and formed of thermoplastic material, the intermediate foil having an edge and upper and lower sides and being simultaneously connected by welding at the lower side with the lower foil and at the upper side with the upper foil only in the region of the edges so that a gas distributing chamber is formed between the upper foil and the intermediate foil, and means for connecting the intermediate foil with the upper foil and means for connecting the intermediate foil with the lower foil, the connecting means being formed so that the connection of the intermediate foil with the upper foil is stronger than the connection of the intermediate foil with the lower foil, so that in a closed condition of a package the intermediate foil extends loosely over the upper foil and is connected with the lower and upper foils only in the region of the edges to form the gas distributing chamber, but upon opening the package the intermediate foil is left at the upper foil.

30 Claims, 5 Drawing Sheets

GAS-STERILIZABLE PACKAGE, COVER OF AND ARRANGEMENT FOR PRODUCING THE SAME

CROSS-REFERENCE TO RELATED APPLICATION

This application is a continuation-in-part of patent application Ser. No. 901,027 filed on Aug. 27, 1986 and now abandoned.

BACKGROUND OF THE INVENTION

The present invention relates to a gas-sterilizable package which has a lower foil of thermoplastic material and formed as a shell, and an upper foil of paper or thin fleece and connected with the lower foil along the edges of the foils by welding or sealing. The invention also relates to a cover for the package, as well as to a method of producing the package.

Packages of the above mentioned general type are known in the art and widely used. They are utilized in particular for packing of tools or objects which are required during operations, and must be kept in sterile condition. The upper foil is composed of paper and thereby of fibers. Sacks are also known which use fibers of synthetic plastic materials, so as to guarantee required gas permeability for sterilization by gas, particularly hot steam. In the known packages the release of welding connections between upper foil and lower foil requires a certain force application, since in many cases the fibers are torn from the upper foil and they remain adhesively connected mainly to the welding connection of the lower foil. In many cases the torn out fibers reach the packed objects. A further danger is that the packed metallic devices, such as the above mentioned tools for an operation, rub during transportation of the packages against the inner surface of the paper or fleece layer and thereby also release the fibers which deposit in many cases on the tools. For eliminating the above mentioned disadvantages it was proposed to apply a wax coating on the paper or fleece layer at their side facing toward the interior of the package. This wax coating has the advantage that it forms a peelable welding connection of the paper or fleece layer with the lower foil and reduces the wear by the metal devices in the sack. However, it also possesses the disadvantage that the wax coating of the foil of paper or fleece considerably affects the gas permeability during gas treatment for the purpose of sterilization or vacuum deep drawing in autoclaves. The considerably reduced permeability can be compensated only by a longer time of the application of the gas treatment which increases the costs of the process. When the gas treatment or the vacuum drawing is performed in a fast cycle, it leads to swelling up and tearing of the sack or similar package.

SUMMARY OF THE INVENTION

Accordingly, it is an object of the present invention to provide a gas-sterilizable package which is simple and reliable in manufacture and which also can be opened in a simple manner despite high strength of the welding connection.

In keeping with these objects and with others which will become apparent hereinafter, one feature of the present invention resides, briefly stated, in a gas-sterilizable package which has a lower foil composed of a thermoplastic material and having an edge, an upper gas-permeable foil having an edge, the lower foil and the upper foil being connected with one another in the region of the edges, an intermediate gas-permeable foil arranged to protect the upper foil from a content of the package, located between the upper and lower foils and loosely extending over the upper foil, the intermediate foil being perforated and formed of thermoplastic material, the intermediate foil having an edge and upper and lower sides and being simultaneosly connected by welding at the lower side with the lower foil and at the upper side with the upper foil only in the region of the edges so that a gas distributing chamber is formed between the upper foil and the intermediate foil, and means for connecting the intermediate foil with the upper foil and means for connecting the intermediate foil with the lower foil, the connecting means being formed so that the connection of the intermediate foil with the upper foil is stronger than the connection of the intermediate foil with the lower foil, so that in a closed condition of a package the intermediate foil extends loosely over the upper foil and is connected with the lower and upper foils only in the region of the edges to form the gas distributing chamber, but upon opening the package the intermediate foil is left at the upper foil.

When the package is formed in accordance with the present invention, an independent intermediate foil of a perforated and therefore considerably gas-permeable plastic material is provided between the upper foil of paper or fleece and the lower foil, whereby a plurality of advantages are achieved. First of all, the upper foil of paper or fleece is protected at its inner side so that the packed tools do not damage the layer of paper or fleece and fibers cannot be removed from it. Further, by selection of the synthetic plastic material in the sense of strength or chemical properties it is possible in a simple manner to provide a simple adaptation to the type of sterilization and also the sequence in which it must be performed to provide an optimal adaptation. For example, the gas permeability can be adjusted by the type of the perforations by means of selection of smaller or greater holes and their distribution so as to achieve the optimal conditions. The type and thickness of the thermoplastic foil can provide adaptation of the desired value of the welding to the optimal conditions.

In accordance with a very important feature of the present invention, the gas-distributing chamber provided between the gas-permeable upper foil and the perforated intermediate foil distributes the gas which has passed through the upper foil. The gas distributing chamber therefore provides several gas streams which pass along the upper surface of the intermediate foil so that the upper surface of the intermediate foil becomes effectively sterilized by the streaming gas flows, that further pass through the holes in the perforated intermediate foil into the package.

The inventive solution also provides for further advantage in that the perforated thermoplastic foil as intermediate foil forms the connection of the upper foil with the lower foil by a single welding step. By the selection and construction on the intermediate foil and/or the upper foil and/or the lower foil it is guaranteed that the welding of the thermoplastic perforated intermediate foil with the upper foil is stronger than the welding with the lower foil.

In accordance with a further feature of the present invention, the thermoplastic perforated intermediate foil provides the connection of the upper foil with the lower foil in a single welding step, and by the selection and construction of the intermediate foil and/or upper foil and/or lower foil it is guaranteed that the welding of the thermoplastic perforated intermediate foil with the upper foil is stronger than the welding with the lower foil.

A further feature of the present invention is that the thermoplastic perforated intermediate foil is connected with the upper foil at certain locations, particularly in point-shaped locations. The point-shaped connection can be achieved by welding or glueing. With this feature the gas permeability of the package is not affected.

This proposal also serves for simplifying the production, since practically a foil composite is produced which includes the upper foil and the loosely connected perforated synthetic plastic intermediate foil. Since the above composite of the upper foil and the perforated thermoplastic intermediate foil is loose, it can be wound, unwound and worked very well in a stress-free manner.

The perforations of the thermoplastic intermediate foil can be made in a simple manner as holes made by heated needle tips or as cuts with cross shapes. The latter mentioned cuts have the advantage that during treatment with gas especially high heated water steam they open and then close after the sterilization or close continuously.

In accordance with the invention, the welding of the thermoplastic perforated intermediate foil with the upper foil is stronger than the welding with the lower foil. As a result of this, the welding of the cover composed of the paper or fleece and the perforated synthetic intermediate foil can be easily released from the lower foil, formed for example, as a shell. This can be achieved in various ways. It is possible to produce the upper foil and the lower foil of such material that the thermoplastic perforated intermediate foil during welding with the upper foil has a stronger welding connection, while with the lower foil has a weaker welding connection. It can be achieved in such a manner that the paper or similar fleece of the upper foil is provided with additional substances or the upper foil is treated so that the welding with the loosely connected perforated intermediate foil is stronger than the welding with the lower foil applied to the other side of the perforated plastic intermediate foil.

The treatment of the additional substances or the selection of the foil layers to be connected with the upper foil and with the perforated intermediate foil is performed in accordance with the basic principle that as a result of these measures the sterilizability of the package is not affected.

In accordance with an especially advantageous feature of the invention, the perforated thermoplastic intermediate foil is coated at its side facing toward the lower foil with a layer which reduces the strength (thickness) of the welding connection with the lower foil. It is especially advantageous when this layer is composed of a thin foil, for example of polyethylene with 2-6% of polybutylene.

In accordance with a further feature of the present invention, the interconnected foils of paper and plastic are offset at one edge of the package relative to the lower foil so as to form a portion which can be grasped by hand for separating the interconnected foils from the lower foil by peeling the foils in the welding or sealing seam from the lower foil.

In accordance with the invention it is advantageous when a web from which lower foils are formed is pressed so as to form a plurality of troughs. It is also possible to provide such packages in which the lower foil is not subjected to thermoplastic deformation, but instead is flat and serves for packing such objects which are substantially flat, for example cutters. In this case the interconnected unit of paper web and perforated synthetic plastic web is connected with the lower foil by a U-shaped welding so as to provide a filling opening. After insertion of the objects, this filling opening is closed by a transversely extending welding seam, so that in general a ring-shaped welding takes place.

It is especially advantageous when in a package the upper foil is composed of paper and the intermediate synthetic plastic foil with perforations is composed of polyethylene, while the lower foil is formed as a composite foil with inner foil layers of polyethylene and outer foil layers of polyamide.

The invention also deals with a method of producing the package which includes means for deep drawing of troughs in a lower foil web, means for filling the troughs with objects, an unwinding device located above the lower foil web for unwinding a synthetic plastic foil, means for perforating the synthetic plastic foil so as to form a plurality of uniformly distributed openings, means for unwinding a paper web, a deviating roller which places the paper web onto the perforated synthetic plastic web, a deviating roller which places the interconnected foils of paper web and synthetic plastic web onto the lower foil web, a welding and separating device which connects by a ring-shaped closed welding seam the interconnected layers of paper web and synthetic plastic web with the lower foil web, and means for separating a finished package from the above mentioned paper web and synthetic plastic web, on the one hand, and the lower foil web, on the other hand.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
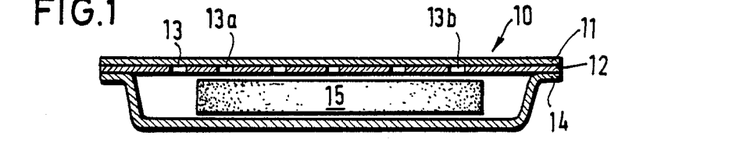
FIG. 1 is a view showing a vertical section of the package in accordance with the present invention.

FIG. 1 shows a package 10. It includes an upper foil 11 of paper or a fleece, and also synthetic plastic fibers. A thermoplastic synthetic foil 12 is further provided and has a plurality of perforations 13, 13a, etc. The package also has a lower foil 14 of a thermoplastic synthetic foil which in the embodiment of FIG. 1 is formed as a deep-drawn shell. Of course it can also be flat.

Figure 1A:
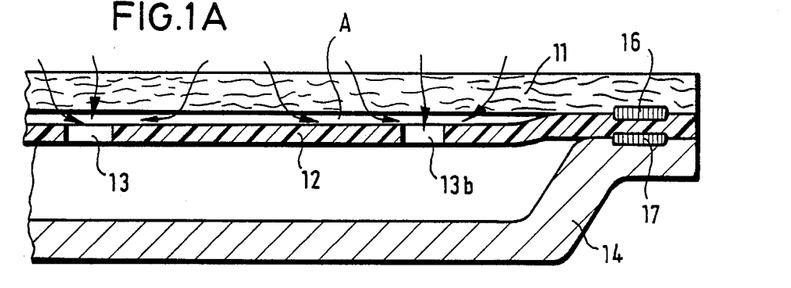
FIG. 1A is a view showing a part of the view of FIG. 1 on an enlarged scale, illustrating a gas distributing chamber of the package in accordance with the present invention.

As can be seen in FIG. 1A the upper foil 11 which is a gas permeable foil, the thermoplastic synthetic intermediate foil 12 which is a perforated foil, a thermoplastic synthetic lower foil 14 are connected with one another only in the region of their edges, as will be explained hereinbelow in detail. With the connection of the upper foil 11 and the intermediate foil 12 only in the region of their edges, a gas distributing chamber A is formed between these foils. During gas sterilization, gas passes through the upper gas permeable foil 11, then distributes in the chamber A, and then passes in several gas streams through the intermediate foil 12. The gas-distributing chamber A thus distributes the gas so that the upper surface of the intermediate foil 12 becomes effectively sterilized by the streaming gas flows, that further pass through the perforations 13, 13a, into the interior of the package. Thus, the chamber between the foils 11 and 12 is a gas-distributing chamber that sterilizes the foil 12 and enables the gas flows to pass over the upper surface of the foil 12 and then through the perforations of the latter.

Figure 2:
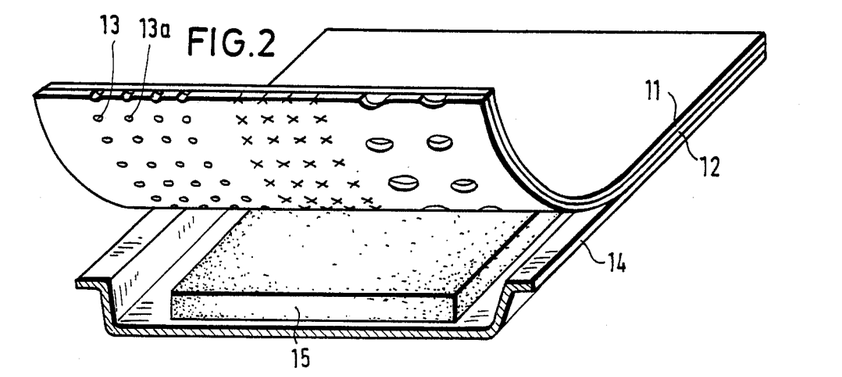
FIG. 2 is a view showing the package of FIG. 1 in a section and in perspective.

FIG. 2 shows the upper foil 11 with the loosely attached intermediate foil 12 of a thermoplastic synthetic material which has a plurality of perforations of different types for the purpose of illustration. The left part of the foil has small round openings. The central part of the foil has cross-shaped cuts. The right part of the foil has greater openings arranged at greater distances from one another. A packed product is identified with reference numeral 15 and often is a working tool.

Figure 3:
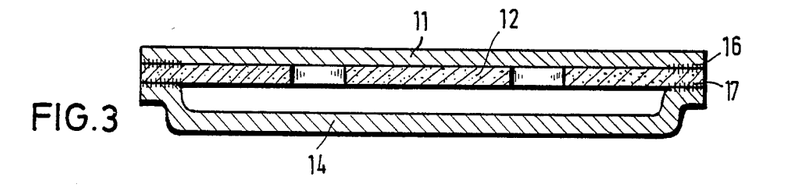
FIG. 3 is a view showing a vertical section of a package in accordance with another embodiment of the present invention.

FIG. 3 shows the foil layers 11, 12 and 14 which are connected by two peripheral end complete welding seams 16 and 17 produced in one welding process. The welding seam 16 connects the upper foil 11 with the perforated intermediate foil 12, while the welding seam 17 connects the perforated intermediate foil 12 with the lower foil 14. The welding seam 16 for peripheral connection of the upper foil with the intermediate foil is stronger than the welding seam 17 for connecting the intermediate foil with the lower foil. Thereby it is guaranteed that, as shown in FIG. 2, the cover layer formed by the foils 11 and 12 can be peeled from the lower foil 14. For obtaining this action, the foils 11 and 14 are selected with respect to the intermediate foil 12, in the embodiment of FIG. 3, in such a manner as to satisfy the above mentioned requirements.

Figure 4:
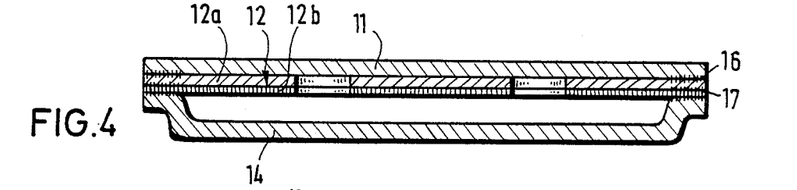
FIG. 4 is a view showing a vertical section of a package in accordance with a further embodiment of the present invention.

Especially advantageous embodiment is shown in FIG. 4, in which the perforated intermediate foil 12 is composed of two foil pairs 12a and 12b. The foil layer 12b is a thin coating with a material which reduces the strength of the welding connection. The layer 12b can be composed for example of polyethylene with the addition of 3-6% of polybutylene. It is then advantageously connected with the foil 12a also of polyethylene, which however does not have the addition of polybutylene or polybutane. Thereby it is guaranteed that the welding 17 is weaker than the welding 16.

Figure 5:
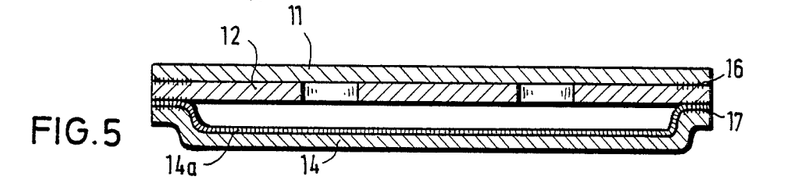
FIG. 5 is a view showing a vertical section of a package in accordance with still a further embodiment of the invention.

FIG. 5 shows the embodiment in which the intermediate foil 12 is a one-piece layer, while the lower foil 14 is provided with a coating 14a which is composed, for example, of polyethylene with a content of 2-6% of polybutylene. Thereby it is also guaranteed that the welding seam 17 is weaker and therefore the cover foil composed of two foils 11 and 12 can be easily peeled from the lower foil for opening of the package.

Figure 6:
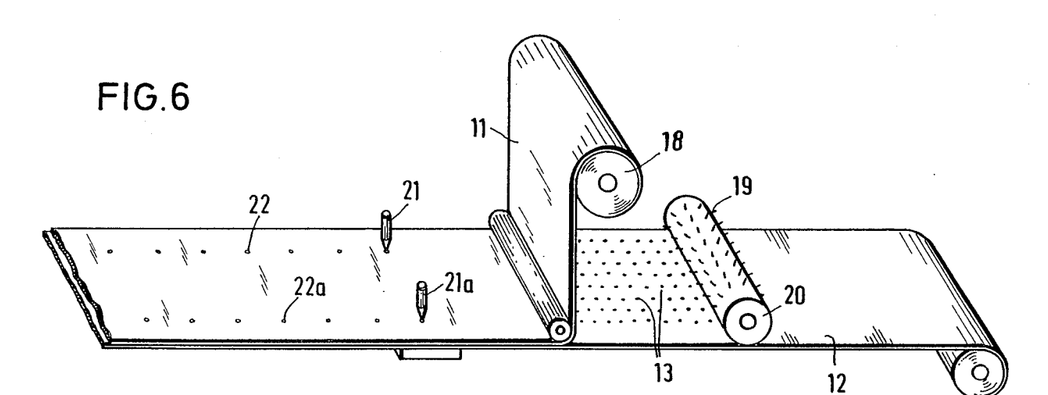
FIG. 6 is a perspective view schematically showing the production of an upper foil with an intermediate foil of the inventive package.

FIG. 6 shows the production of the cover foil composed of the foil 11 of paper or fleece and wound out from a roll 18. It is applied onto the synthetic plastic foil 12 which is continuously provided with perforations by a roller having a plurality of thorns or spikes 19. The upper foil 11 and the lower foil 12 are connected in a pointed manner by heated pins 21 and 21' in association with a counter support. Thereby they are loosely connected by weld spots 22 and 23. Also, a point-like or other local adhesion can be provided at certain locations. Thereby, a connection is formed which does not affect the required gas permeability and at the same time guarantees that the foil composite 11 and 12 can be easily worked.

Figure 7:
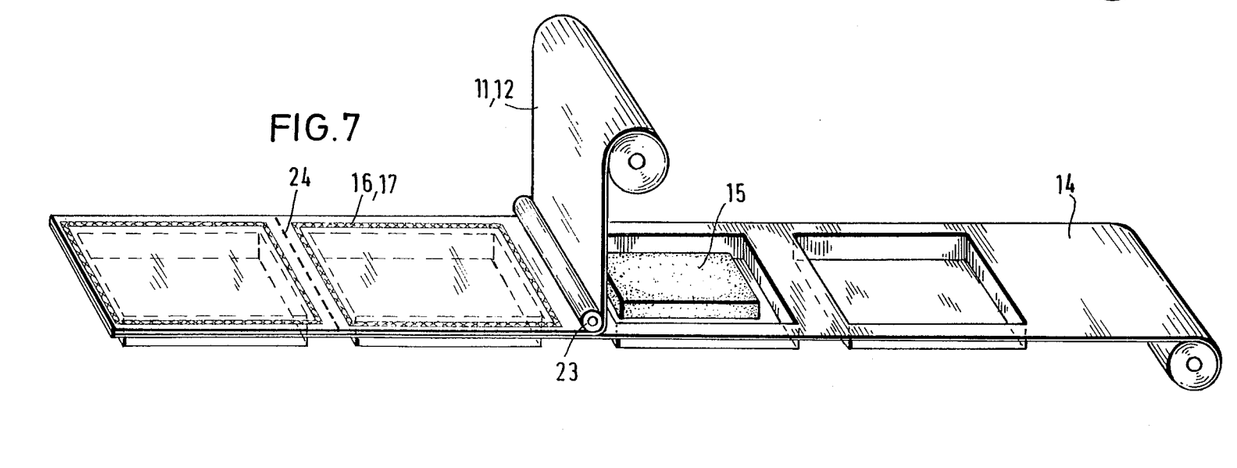
FIG. 7 is a perspective view schematically showing the production of a package of the invention.

FIG. 7 shows the deformation of the lower foil 14 so as to form a plurality of troughs into which a product 15 can be automatically introduced. The foil composite 11, 12 is supplied by a deviating roller 23 and provided with the peripheral welding seams 16, 17. Finally, a transverse separating cut 24 is formed especially in form of a tearable perforation. After this, the band is fed to an autoclave for sterilization.

From FIG. 7 it can be clearly seen that the deformation of the lower foil, the introduction of the object, and the closing with the double-layer cover foil are performed automatically.

Figures 8, 9, 10:
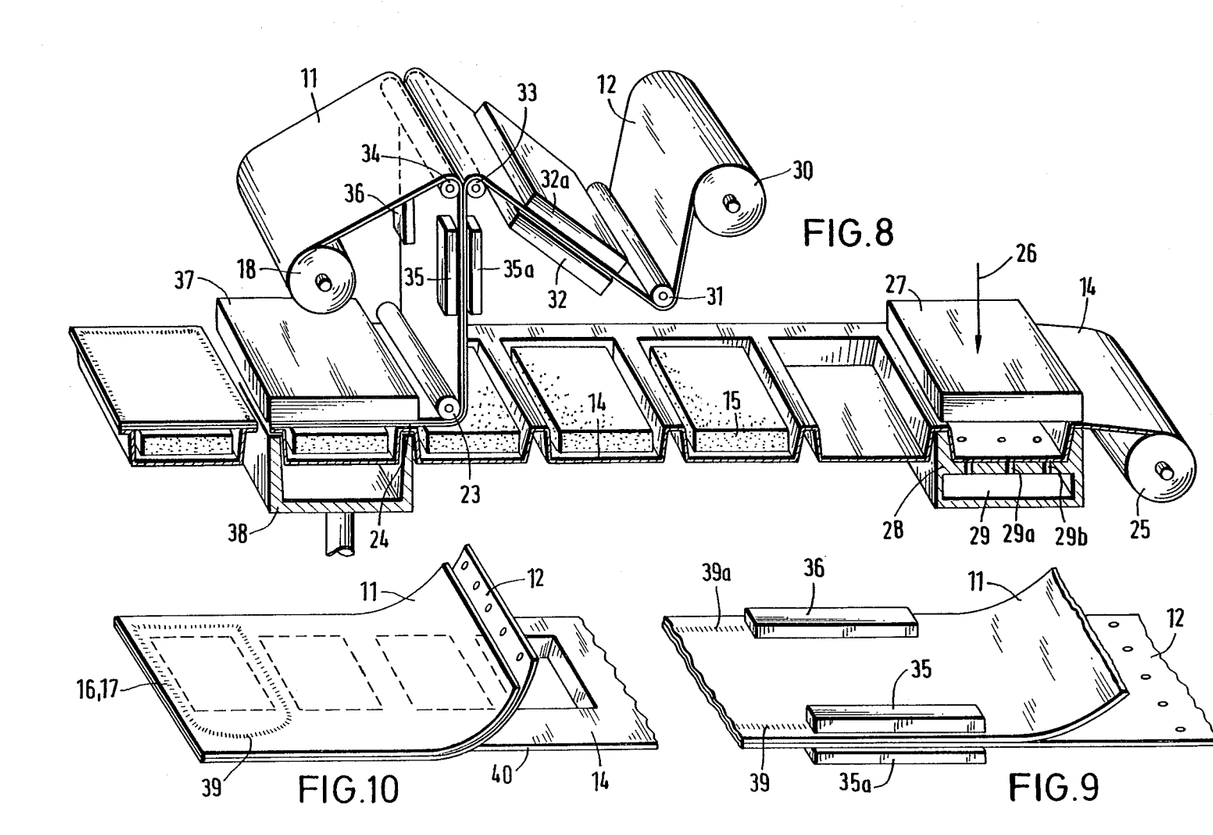
FIG. 8 is a perspective view, partially set in section, showing an arrangement for producing packages with a deep-drawn lower foil in accordance with the invention.
FIGS. 9 and 10 are views showing sections of the arrangement of FIG. 8, on the enlarged scale.

FIG. 8 shows the supply roller of the lower foil 14. The lower foil is fed to a forming station 26 which includes a cover plate 27 and a lower dye 21. The lower foil is deformed to form troughs by means of a negative pressure chamber 29 in cooperation with sieve-shaped openings 29a, 29b, etc. A filling device which is known per se and not shown in the drawing, fills the objects to be packed into the associated troughs. A supply roller 30 for the synthetic plastic foil is arranged above the web with the troughs. The synthetic plastic foil is supplied via a deviating roller 31, which can also be formed as a driving roller, through a perforating device 32, 32a shown in FIG. 6 and formed for example as a roller provided with a thorn 19. The perforated synthetic plastic foil web is guided over a deviating roller 33 downwardly.

The roller 33 cooperates with a roller 34 which also leads downwardly the paper web 11 wound from the roller 18. It is advantageous when the rollers 33 and 34 are formed as pulling rollers, and this roller pair 33, 34 is driven. Furthermore, it is advantageous when this roller pair is provided with a common drive, so that the uniform supply of the paper web 11 and the perforated foil web 12 is guaranteed.

Welding bars 35, 35a and 36, 36a (the latter is not visible in the drawings) are arranged under the roller pair 33, 34 at a distance from one another. The roller bars connect the paper web 11 and the perforated synthetic plastic foil 12 by welding in the region of the side edges.

The foil composite 11, 12 arrives via a deviating roller 23 at the lower web 14 which is filled with the objects. A welding device which is composed of an upper welding bar 37 and a lower U-shaped or box-shaped welding bar 38 operates for producing the welding seam 16, 17 formed as a rectangular ring described in FIG. 7. Simultaneously, the transverse cut-out 24 is also produced as described with reference to FIG. 7.

FIG. 9 shows the foil composite 11 and 12 with the welding seams 39, 39a which are formed by means of the welding bars 35a, 35 and 36 at the edges of the composite. These welding seams are located in a region which is inoperative in the finished package and thereby can be absent since the welding seam which is closed to form a ring in FIG. 8 or the U-shaped welding seam which will be described in reference to FIG. 11 later on, connects the paper web with the perforated synthetic plastic foil web, and simultaneously with the lower foil 14 by welding, so as to form the finished filled package of FIG. 8, or not filled package of FIG. 11 with a sufficient safety of the foil layers.

The connection by means of the welding bars 35 and 36 in the edge zones of the paper web 11 and the perforated foil web 12 is performed as shown in FIG. 9 in the case when the foil composite is a sales item and is transported. When, however, as shown in FIG. 8, the device for supplying the lower foil web 14 and simultaneously the foil webs 11 and 12 is a spatial unit, then welding or sealing or glueing of the paper web 11 with the perforated synthetic plastic foil web 12 is not necessary, since the welding seams 16 and 17 for forming the finished package or a package provided with filling openings sufficiently secure the foil layers 11 and 12, on the one hand, and the lower foil web 14, on the other hand, in their position.

FIG. 10 shows that the foil composite 11, 12 is placed onto the lower foil web 14 provided with troughs and after introduction of the filling objects 15 is provided with welding seams 16 and 17 in form of a closed ring. FIG. 10 also shows that the coil composite 11, 12 extends at one edge outwardly beyond the lower foil 14, and the apex point 39 of the welding seam 16, 17 is spaced at a distance from an edge 40 of the lower foil web 14, so that the foil web 14 on the one hand and the foil composite 11, 12 on the other hand, can be individually engaged by hand. Therefore, the package can be opened by peeling in the weld connection 16, 17 by means of lifting of the foil composite 11, 12 from the lower web 14.

Figure 11:
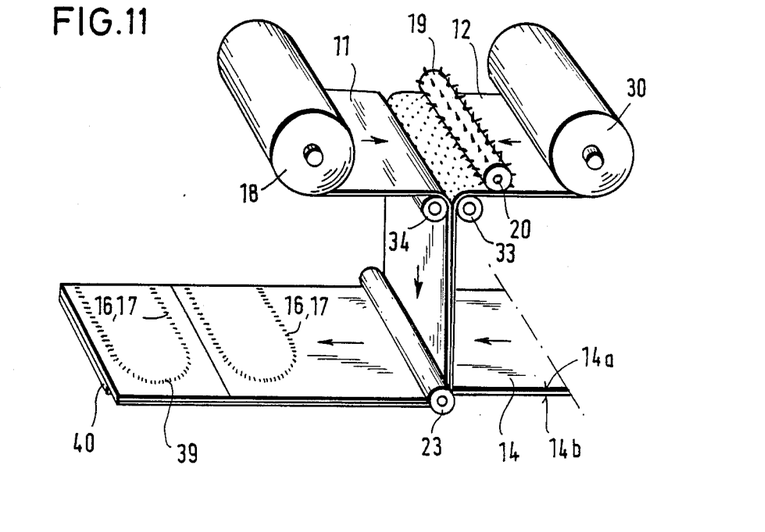
FIG. 11 is a view showing an arrangement for producing a package with flat lower foils.

FIG. 11 shows the supply roller 30 of the synthetic plastic foil web 12 in connection with the roller 20 which is provided with the thorns 19 as shown in FIG. 6, for producing openings in the foil web 12. Reference numeral 18 identifies the supply roller of the paper web 11. The webs 11 and 12 are wound out from both rollers 18 and 30 over the pulling roller pair 33, 34. The welding device 35, 35a, and 36, 36a for connecting the webs 11 and 12 is not shown in FIG. 11. It is not needed here since both webs are supplied to the deviating roller 23 of the lower web 14 and then connected with the lower web 14 by the U-shaped welding seam 16, 17. FIG. 11 also shows that the web composite 11, 12 extends outwardly beyond the lower web 14 at one longitudinal edge. Furthermore, it is shown here that the apex point 39 of the U-shaped welding seam 16, 17 is spaced from the edge 40 of the lower foil 14. This is shown more clearly and on a larger scale in FIG. 12. Thereby the composite 11, 12 on the one hand, and the lower foil 14, on the other hand, can be easily engaged by hand and therefore the weld connection 16, 17 can be released by peeling.

Figure 12:
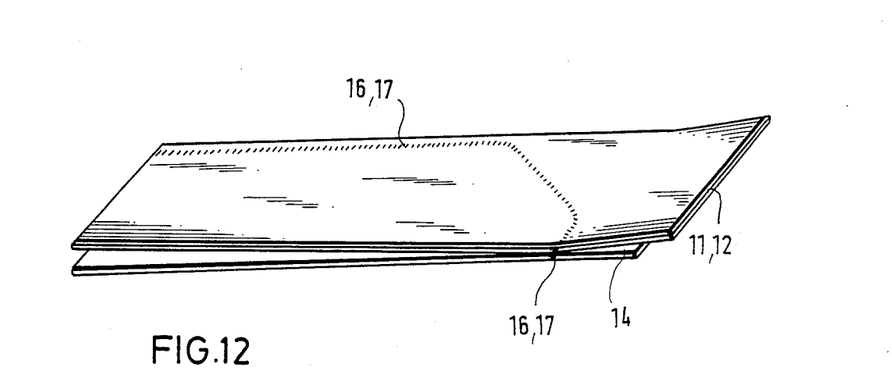
FIG. 12 is a view showing a package in accordance with a further embodiment of the invention, partially in section.

FIGS. 11 and 12 also show that the lower foil 14 is composed of two foil layers, namely the inner foil layer 14a of polyethylene and the outer foil layer 14b of polyamide.

It will be understood that each of the elements described above, or two or more together, may also find a useful application in other types of constructions differing from the types described above.

While the invention has been illustrated and described as embodied in a gas-sterilizable package, and a cover foil and an arrangement for producing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A package to be gas-sterilizable, comprising a lower foil composed of a thermoplastic material and having an edge; an upper gas-permeable foil having an edge, said lower foil and said upper foil being connected with one another in the region of said edges; an intermediate gas-permeable foil arranged to protect said upper foil from a content of the package, located between said upper and lower foils and loosely extending over said upper foil, said intermediate foil being perforated and formed of thermoplastic material, said intermediate foil having an edge and upper and lower sides and being simultaneosly connected by welding at said lower side with said lower foil and at said upper side with said upper foil only in the region of said edges so that a gas distributing chamber is formed between said upper foil and said intermediate foil; and means for connecting said intermediate foil with said upper foil and means for connecting said intermediate foil with said lower foil, said connecting means being formed so that the connection of said intermediate foil with said upper foil is stronger than the connection of said intermediate foil with said lower foil, so that in a closed condition of a package said intermediate foil extends loosely over said upper foil and is connected with said lower and upper foils only in the region of said edges to form said gas distributing chamber, but upon opening the package said intermediate foil is left at said upper foil.

2. A package as defined in claim 1, wherein said upper foil is composed of a material selected from the group consisting of paper and fleece, said lower foil being composed of a thermoplastic material.

3. A package as defined in claim 1, wherein said lower foil is shell-shaped.

4. A package as defined in claim 1, wherein said connecting means is welding means which connect said intermediate foil with said upper and lower foils.

5. A package as defined in claim 1, wherein said connecting means is sealing means for connecting said intermediate foil with said upper and lower foils.

6. A package as defined in claim 1, wherein said connecting means includes means for connecting said intermediate foil with said upper foil in a plurality of points.

7. A package as defined in claim 6, wherein said means for connecting said intermediate foil with said upper foil in a plurality of points is formed as welding means.

8. A package as defined in claim 6, wherein said means for connecting said intermediate foil with said upper foil in a plurality of points is formed as adhesive means.

9. A package as defined in claim 1, wherein said intermediate foil is formed with a plurality of perforations which are formed as holes and occupy a greater part of said intermediate foil.

10. A package as defined in claim 1, wherein said connecting means is formed so that the connection of said intermediate foil with said upper foil is stronger than the connection of said intermediate foil with said lower foil.

11. A package as defined in claim 10, wherein said means for connecting said intermediate foil with said upper foil and with said lower foil are welding means.

12. A package as defined in claim 11, wherein said intermediate foil has a first intermediate foil layer facing toward said upper foil and a second intermediate foil layer facing toward said lower foil and coating said first intermediate foil layer so as to reduce the strength of the welding means which connect said intermediate foil with said lower foil.

13. A package as defined in claim 11, wherein said lower foil has a first lower foil layer, and a second lower foil layer which faces toward said intermediate foil and coats said first lower foil layer so as to reduce the strength of the welding means for connecting said lower foil with said intermediate foil.

14. A package as defined in claim 12, wherein said second intermediate foil layer is formed as a thin foil composed of polyethylene with 2-6% of polybutylene.

15. A package as defined in claim 13, wherein said second lower foil layer is formed as a thin foil composed of polyethylene with 2-6% of polybutylene.

16. A package as defined in claim 1, wherein said upper foil and said intermediate foil are arranged on said lower foil so that they are offset relative to at least one edge of the lower foil so as to form a portion which is engageable by hand for separating said upper foil with said intermediate foil by peeling from said lower foil.

17. A package as defined in claim 1, wherein said lower foil is formed as a flat web, said upper foil and said intermediate foil being connected with said flat web by a U-shaped welding seam.

18. A package as defined in claim 1, wherein said upper foil is composed of paper, said intermediate foil provided with perforations is composed of polyethylene, said lower foil being composed of a composite foil having a plurality of foil layers, said foil layers including an inner foil layer composed of polyethylene and an outer foil layer composed of polyamide.

19. A package to be gas-sterilizable, comprising a lower foil and having an edge; an upper gas-permeable foil having an edge, said lower foil and said upper foil being connected with one another in the region of said edges; an intermediate gas-permeable foil arranged to protect said upper foil from a content of the package, located between said upper and lower foils and loosely extending over said upper foil, said intermediate foil being perforated and having an edge and upper and lower sides and being connected at said lower side with said lower foil and at said upper side with said upper foil in the region of said edges so that a gas distributing chamber is formed between said upper foil and said intermediate foil; and means for connecting said intermediate foil with said upper foil and means for connecting said intermediate foil with said lower foil, said connecting means being formed so that the connection of said intermediate foil with said upper foil is stronger than the connection of said intermediate foil with said lower foil, so that in a closed condition of a package said intermediate foil extends loosely over said upper foil and is connected with said lower and upper foils only in the region of said edges to form said gas distributing chamber, but upon opening the package said intermediate foil is left at said upper foil.

20. A cover for producing a package to be gas-sterilized, and having a lower foil composed of a thermoplastic material and having an edge; an upper gas-permeable foil having an edge, the cover comprising a cover foil including an upper gas-permeable foil layer having an edge, and an intermediate gas-permeable foil arranged to protect said upper foil from a content of the package to be located between said upper foil layer and said lower foil layer and having an edge, said intermediate foil being composed of thermoplastic material said intermediate foil layer extending over and being connected with said upper foil layer at a plurality of locations, only in the region of said edges so that a gas distributing chamber is formed between said upper foil layer and said intermediate foil layer, and connecting means for connecting said intermediate foil layer with said upper foil layer at the plurality of locations only in the region of said edges; and means for connecting said intermediate foil with said upper foil and means for connecting said intermediate foil with said lower foil, said connecting means being formed so that the connection of said intermediate foil with said upper foil is stronger than the connection of said intermediate foil with said lower foil, so that in a closed condition of a package said intermediate foil extends loosely over said upper foil and is connected with said lower and upper foils only in the region of said edges to form said gas distributing chamber, but upon opening the package said intermediate foil is left at said upper foil.

21. A cover as defined in claim 20, wherein said connecting means for connecting said intermediate foil layer with said upper foil layer is welding means.

22. A cover as defined in claim 20, wherein said connecting means for connecting said intermediate foil layer with said upper foil layer is adhesive means.

23. A cover as defined in claim 20, wherein said upper foil layer is composed of a material selected from the groups consisting of paper and fleece.

24. A cover for producing a package to be gas-sterilized and having a lower foil with an edge, the cover comprising a cover foil including an upper gas-permeable foil layer having an edge, and an intermediate gas-permeable foil layer arranged to protect said upper foil from a content of the package to be located between said upper foil layer and said lower foil and having an edge, said intermediate foil being composed of thermoplastic material and provided with a plurality of perforations, said intermediate foil layer loosely extending over and being connected with said upper foil layer at a plurality of locations, only in the region of said edges so that a gas distributing chamber is formed between said upper foil layer and said intermediate foil layer, and connecting means for connecting said intermediate foil layer with said upper foil layer at the plurality of locations only in the region of said edges; and means for connecting said intermediate foil with said upper foil and means for connecting said intermediate foil with said lower foil, said connecting means being formed so that the connection of said intermediate foil with said upper foil is stronger than the connection of said intermediate foil with said lower foil, so that in a closed condition of a package said intermediate foil extends loosely over said upper foil and is connected with said upper and lower foils only in the region of said edges to form said gas distributing chamber, but upon opening the package said intermediate foil is left at said upper foil.

25. An arrangement for producing a package to be gas-sterilizable and composed of a lower foil having an edge, an upper foil having an edge and connected with the lower foil in the region of the edges, and a perforated thermoplastic intermediate foil connected with the upper foil and the lower foil, the arrangement comprising means for supplying a lower foil web; means for applying an upper foil web with an intermediate foil web onto the lower foil web; means for connecting the upper foil web and the intermediate foil web so as to form a gas-distributing chamber therebetween and also with the lower foil web by a peripheral enclosed welding seam so as to form a plurality of the packages each including the upper, intermediate and lower foils with the gas-distributing chamber between the upper and intermediate foils; and means for separating the packages from the webs.

26. An arrangement as defined in claim 25; and further comprising means for forming in the lower foil web a plurality of trough-shaped shells.

27. An arrangement as defined in claim 25; and further comprising means for filling the shells with objects prior to the applying of the upper and intermediate foil webs onto the lower foil web; means for unwinding the intermediate foil web; means for perforating the intermediate foil web unwound by said unwinding means; means for unwinding the upper foil web; means for applying the unwound upper foil web onto the perforated intermediate foil web located before said means for applying the upper foil web and the intermediate foil web onto the lower foil web.

28. An arrangement as defined in claim 25; and further comprising means for connecting the upper foil web with the intermediate foil web in the region of longitudinal side edges of the upper foil web and the intermediate foil web.

29. An arrangement as defined in claim 28, wherein said connecting means for connecting said upper foil web with the intermediate foil web is welding means.

30. An arrangement as defined in claim 28, wherein said connecting means for connecting said upper foil web with the intermediate foil web is sealing connecting means.

* * * * *

REEXAMINATION CERTIFICATE (1509th)
United States Patent [19]
Sengewald

[11] B1 4,884,694
[45] Certificate Issued  Jul. 9, 1991

[54] GAS-STERILIZABLE PACKAGE, COVER OF AND ARRANGEMENT FOR PRODUCING THE SAME

[76] Inventor: Karl-Heinz Sengewald, 4802 Halle, Westf. 1, Fed. Rep. of Germany

Reexamination Request:
  No. 90/002,073, Jun. 28, 1990
  No. 90/002,126, Sep. 7, 1990

Reexamination Certificate for:
  Patent No.: 4,884,694
  Issued: Dec. 5, 1989
  Appl. No.: 213,615
  Filed: Jun. 30, 1988

Related U.S. Application Data

[63] Continuation-in-part of Ser. No. 901,027, Aug. 27, 1986, abandoned.

[30] Foreign Application Priority Data

Aug. 27, 1985 [DE] Fed. Rep. of Germany ....... 3530484
Aug. 12, 1986 [DE] Fed. Rep. of Germany ....... 3623568

[51] Int. Cl.$^5$ ............................................. B65D 5/64
[52] U.S. Cl. ............................ 206/484.1; 206/484.2; 206/439; 206/524.2; 206/524.4; 206/631; 428/354; 428/34.2; 428/34.3

[56] References Cited
U.S. PATENT DOCUMENTS
4,367,816  1/1983  Wilkes ................................ 206/439

*Primary Examiner*—William I. Price

[57] ABSTRACT

A package to be gas-sterilizable comprises a lower foil composed of a thermoplastic material and having an edge, an upper gas-permeable foil having an edge, the lower foil and the upper foil being connected with one another in the region of the edges, an intermediate gas-permeable foil arranged to protect the upper foil from a content of the package, located between the upper and lower foils and loosely extending over the upper foil, the intermediate foil being perforated and formed of thermoplastic material, the intermediate foil having an edge and upper and lower sides and being simultaneously connected by welding at the lower side with the lower foil and at the upper side with the upper foil only in the region of the edges so that a gas distributing chamber is formed between the upper foil and the intermediate foil, and means for connecting the intermediate foil with the upper foil and means for connecting the intermediate foil with the lower foil, the connecting means being formed so that the connection of the intermediate foil with the upper foil is stronger than the connection of the intermediate foil with the lower foil, so that in a closed condition of a package the intermediate foil extends loosely over the upper foil and is connected with the lower and upper foils only in the region of the edges to form the gas distributing chamber, but upon opening the package the intermediate foil is left at the upper foil.

FIG.1A

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-30 are cancelled.

* * * * *